United States Patent [19]
Van Doorn et al.

[11] Patent Number: 5,529,901
[45] Date of Patent: Jun. 25, 1996

[54] METHOD FOR DETERMINING THE PRESENCE OR AMOUNT OF ANALYTE USING A STABLE COLLOIDAL CARBON SOL

[75] Inventors: Albert W. J. Van Doorn, Arnhem; Jan H. Wichers, Wageningen; Wilhelmus M. J. Van Gelder, Zetten, all of Netherlands

[73] Assignee: Staat der Nederlanden, Wageningen, Netherlands

[21] Appl. No.: 241,734

[22] Filed: May 12, 1994

Related U.S. Application Data

[63] Continuation-in-part of Ser. No. 778,784, Oct. 18, 1991, abandoned, which is a continuation-in-part of Ser. No. 273,258, Nov. 18, 1988, abandoned.

[30] Foreign Application Priority Data

Nov. 19, 1987 [NL] Netherlands ............................ 8702769

[51] Int. Cl.$^6$ ...................................................... C12Q 1/68
[52] U.S. Cl. .................. 435/6; 435/7.1; 435/7.2; 435/962; 435/970; 436/518; 436/524; 436/810; 252/302
[58] Field of Search .............................. 252/302; 435/6, 435/7.1, 962, 970; 436/518, 524, 810

[56] References Cited

FOREIGN PATENT DOCUMENTS 0321008  6/1989  European Pat. Off. .

OTHER PUBLICATIONS

T. Waller, "The india-ink immunoreaction: a method for the rapid diagnosis of encephalitozoonosis"; Laboratory Animals (1977) II, 93–97.

P. Geck, "India–Ink Immuno–Reaction for the Rapid Detection of Enteric Pathogens"; Acta microbiol. Acad. Sci. hung. 18: 191–196 (1971).

N. R. Berguist et al, "A Novel Simple Immunoassay for Rapid Detection of Human IgG antibodies to *Toxoplasma gondii*"; J. Immunolog. Method, 61: 339–344 (1983).

*Primary Examiner*—Toni R. Scheiner
*Assistant Examiner*—Susan C. Wolski
*Attorney, Agent, or Firm*—Cooper & Dunham

[57] ABSTRACT

This invention relates to a method for determining the presence or amount of an analyte in a sample comprising contacting the sample with a labeled constituent consisting of an aqueous carbon sol which is stable in the absence of a stabilizing substance. The colloidal carbon particles have directly conjugated to their surface a binding component which specifically binds to the analyte and the resulting analyte/carbon particle complex is used as an indication of the presence or amount of analyte in the sample. The grade of carbon used satisfies the condition V>0 wherein V is a linear predictor value according to the formula
$V = -138.954 - 0.987 \times DBP + 15,609 \times VC + 3.994 \times PPD$,
wherein DBP is the dibutylphthalate adsorption in ml/100 g, as determined according to DIN 53601; VC is the volatile content in %, as determined according to DIN 53552; and PPD is the average primary particle diameter in nanometers.

9 Claims, No Drawings

METHOD FOR DETERMINING THE PRESENCE OR AMOUNT OF ANALYTE USING A STABLE COLLOIDAL CARBON SOL

This application is a continuation-in-part of application Ser. No. 778,784 filed Oct. 18, 1991, now abandoned, which is a continuation-in-part of application Ser. No. 273,258 filed Nov. 18, 1988, now abandoned.

BACKGROUND OF THE INVENTION

This invention relates to a method for determining in a test sample one or more components of the reaction between a specifically-binding protein and the corresponding bindable substance, using the mutual reactivity of such components and of at least one labelled component obtained by coupling or adsorbing particles of a sol of the label directly to the component, comprising during, or after the completion of, the reaction, optionally after the separation of the bound and the free labelled component, determining in said test sample, or in one of the fractions obtained after separation, the presence and/or the quantity of the label by a method suitable for the purpose to obtain a qualitative or quantitative indication of the component to be determined.

The invention further relates to a method of preparing a labelled component of the reaction between a specific binding protein and the corresponding bindable substance by coupling or adsorbing particles of a sol of the label directly to the component, and to a test kit for use in the determination of an immuno component in an aqueous test sample.

As used herein, the phrase "component of the reaction between a specific binding protein and the corresponding bindable substance" means substances, or parts thereof, such as receptor proteins and antigenic determinants, which may be present at the surface of cells, and immuno chemical substances, such as haptens, antigens, and antibodies, which may be present in various media, in particular body fluids, such as blood plasma, serum, and the like or culturing media of cells.

The invention is accordingly concerned with a plurality of fields of histology, such as tissue and cell staining, in which immunochemical reactions take place, but also couplings or adsorptions may take place between the colloidal label and other (macro)molecular structures, such as enzymes, streptavidin, DNA and/or RNA, etc. In addition to these fields, the invention is also concerned with the field of immunoassays for, e.g., diagnostic purposes (determination of antibodies, antigens or haptens in aqueous test samples).

In the part of the specification which follows, the invention will be described in more detail with particular reference to the application of the invention to the field last mentioned, i.e., diagnostic immunoassays, but the invention should not be construed as being limited to such application, as it is equally applicable to histological and histochemical examination methods.

In EP-A-0007654, a survey is given of known immunochemical methods in which the presence of a given immunological component is determined qualitatively and/or quantitatively, using the mutual reactions between such components, such as the reaction between antigen and the antibody against it. These known methods each have certain disadvantages or drawbacks which, according to the above European patent application, can be removed by using, in a method as described above in the opening paragraph, a metal-labelled component, obtained by coupling or adsorbing the component directly or indirectly to particles of an aqueous dispersion of a metal or metal compound or of polymer nuclei coated with a metal or metal compound, with the particles having a size of 6–100 nm.

The metal-immunochemical technique described is more sensitive than the known radio- and enzyme-immunotechniques, and in addition renders it possible to demonstrate and determine more than one immunological component in the same test medium simultaneously by using different metal labels.

The metal sols may be of metals, or metal compounds, such as metal oxides, metal hydroxides or metal salts. As examples are mentioned the metals or metal compounds of gold, silver, iron, nickel, aluminum, chromium, lead, vanadium, mercury, manganese, and generally all those metals which can be readily demonstrated by means of known techniques. Sols of metals are, for example, those of silver, gold and platinum. Sols of metal compounds are, for example, those of silver iodide, iron oxide, aluminum hydroxide, chromium hydroxide, vanadium oxide, iron hydroxide, manganese hydroxide and mercury sulfide.

Preferably, metals or metal compounds are used which do not occur in the test medium, and of these specifically those which can be demonstrated with a selected technique in as low a concentration as possible.

In EP-A-0032270, a survey is given of the possibilities of a qualitative and/or quantitative determination of an immunochemical component, in which one or more labelled components are used which have been obtained by directly or indirectly coupling such a component or components to particles of an aqueous dispersion of a hydrophobic dye or pigment, or of polymeric nuclei coated with such a dye or pigment.

U.S. Pat. No. 4,760,030 (Peterson et al.) discloses a method for determining the presence of a specific binding pair member (sbp member) in a sample. The method involves an agglutination assay using opaque particles capable of agglutinating in the presence of the sbp member. The opaque particles may be derived from carbon particles having a particle size of from 0.2 to 5.0 microns. The carbon particles are conjugated to a specific binding partner of the sbp member to render them capable of agglutinating in the presence of the sbp member. For example, if the sbp member to be determined (i.e. "the analyte") is rheumatoid factor (i.e. a heterogeneous population of auto-antibodies binding to the Fc portion of IgG), a suspension containing carbon particles and IgG is prepared. The test result is read by comparing the optical density (measured at a wavelength of 350 to 800 nm) of the assay medium after the test with the optical density of the assay medium before the agglutination test. A change of optical density indicates the presence of the analyte in the sample. In order to avoid self-agglutination of the carbon particles, they are suspended in an aqueous solution of an amino acid, such as glycine, before coating them with the specific binding partner of the sbp member, and the assay is carried out in an assay medium which contains such an amino acid in an amount sufficient to reduce self-agglutination of the opaque particles.

Also U.S. Pat. No. 5,252,496 (Kang et al.) teaches to subject the carbon particles to a pretreatment with stabilizing agents such as polyalkylene glycol or polysaccharides like dextran to maximize the dispersability of the carbon particles in aqueous media. After this pretreatment with a stabilizing agent, the sbp member is linked to the carbon particle/stabilizing agent complex via a semi-covalently linking reagent such as, e.g., fluorescein-isothiocyanate. The resulting immunochemical label has to be treated subsequently with at least one ionic or non-ionic surfactant in order to render the label suspendable in an aqueous medium such as water or a buffer of low ionic strength.

Bergquist and Waller, J. Immunol. Meth. 61, 339–344 (1983) disclose a carbon immunoassay (CIA) using carbon particles as contained in India ink to determine the presence, if any, of IgG antibodies in a sample. India ink has specific binding characteristics. It binds, e.g., to rabbit IgG and can be used, therefore, in an assay to detect rabbit IgG antibodies to a particulate antigen. It also binds to the membranes of staphylococci. Said membranes contain protein A which is known to bind human IgG antibodies. These properties can be utilized for a rapid detection of human IgG antibodies to the parasite *Toxoplasma gondii*. The test comprises mixing active India ink with protein A to prepare a labelled reagent which is then mixed with *T. gondii* tachyzoites (functioning as the particulate antigen) and a sample suspected of containing human IgG antibodies to *T. gondii*. The test result may be read under a light microscope. The *T. gondii* tachyzoites appear black due to adherent carbon particles in the case of a positive CIA reaction, and otherwise remain white. The CIA test is quite insensitive and claimed to be attractive only because of its simplicity.

SUMMARY OF THE INVENTION

Surprisingly, it has now been found that essentially non-stabilized colloidal carbon particles can be used as a label, and that such particles have advantages over and above the use of other labels.

The method according to the present invention therefore is a method for determining the presence or amount of an analyte in a sample comprising contacting said sample with a labeled constituent consisting of an essentially non-stabilized aqueous carbon sol having directly conjugated to the surface of the colloidal carbon particles a binding component capable of specifically recognizing said analyte and determining the presence or absence of a resulting analyte/carbon particle complex as an indication of the presence or a measure of the amount of analyte in said sample.

DETAILED DESCRIPTION OF THE INVENTION

The words "essentially non-stabilized aqueous carbon sol" or "essentially non-stabilized colloidal carbon particles" refer to a carbon sol in an aqueous medium, such as pure water or water containing a buffer system of low ionic strength, which carbon sol does not require any added stabilizing agent to be stable and preferably does not contain any stabilizing agent. The words "essentially non-stabilized" intend to cover aqueous carbon sols containing a substance which may have a sol-stabilizing effect but are stable also in the absence of said substance. Most preferably, however, said essentially non-stabilized aqueous carbon sol does not contain sol-stabilizing agent.

Surprisingly, we have found that it is possible to predict in a reliable manner whether a certain carbon grade is suited to act as starting material for the preparation of an essentially non-stabilized aqueous carbon sol or not. Said prediction can be made on the basis of three different though related parameters, which characterize the carbon type in question.

The first of said three parameters is the dibutylphthalate adsorption according to DIN53601 (DBP, in ml/100 g) as a measure of secondary particle structure.

The second parameter is the Volatile Content (VC, in %), which is determined by maintaining the carbon sample at a temperature of 950° C. for 7 minutes according to DIN53552. A high volatile content indicates surface oxidation with many polar groups.

The third parameter is the average primary particle diameter (PPD, in nanometers), which is calculated from the number and size measurements taken under the electron-microscope.

The probability that a carbon grade is readily dispersible in aqueous media can be modelled as a function of the parameters DBP, VC and PPD using a Generalized Linear Model. Because the dispersibility is measured as a binary variable (carbon grades are either readily dispersible or not dispersible), the stochastic part of the model is assumed to follow a binomial distribution (McCullagh, P., and J. A. Nelden, Generalized Linear Models, 2nd edition, 1989, Chapter 4 (Chapman and Hall, isbn 0-412-31760-5)). The model was fitted to the data using the statistical computer package Genstar (Payne, R. W. and P. W. Lane (eds.), 1987, Genstar 5 Reference Manual, Clarendon Press, Oxford).

The estimated model formula for the linear predictor value (V) is: $V=-138.954-0.987\times DBP+15.609\times VC+3.994\times PPD$.

A positive linear predictor value (V>0) of certain carbon type indicates that it is suited to act as a starting material for the preparation of essentially non-stabilized aqueous carbon sols (Dispersibility=1; present invention). Carbon grades with a linear predictor value $V\leq 0$ (dispersibility=0) do not form a stable colloidal suspension in aqueous media by themselves. These latter carbon grades therefore need the addition or presence of stabilizing agents in order to form stabilized aqueous carbon sols (Peterson et al., Bergquist and Waller, Kang et al.).

Kang et al use e.g. Cabot carbon grades with V-values between −28.90 and −171.40, indicating that their carbon types are not suited to prepare an essentially non-stabilized aqueous carbon sol. The carbon grades we use all have V-values>0.

The following table shows the distribution of several carbon grades into dispersibility=1 carbons (readily dispersible in aqueous media, i.e. essentially non-stabilized) and dispersibility=0 carbons (not dispersible in aqueous media) on the basis of both experimental data and predicted values (V and dispersibility).

TABLE

| Carbon grade | experimental results dispersibility | V | predicted results dispersibility |
|---|---|---|---|
| Degussa | | | |
| Farbruss FW200 | 1 | 100.51 | 1 |
| Farbruss FW2 | 1 | 35.20 | 1 |
| Farbruss FW1 | 0 | −161.17 | 0 |
| Spezial schwarz SS6 | 1 | 51.99 | 1 |
| Spezial schwarz SS5 | 1 | 46.76 | 1 |
| Spezial schwarz SS4 | 1 | 78.66 | 1 |
| Printex 150T | 1 | 19.46 | 1 |
| Printex 95 | 0 | −111.63 | 0 |
| Spezial schwarz SS550 | 0 | −32.83 | 0 |
| Spezial schwarz SS350 | 0 | −24.48 | 0 |

TABLE-continued

| Carbon grade | experimental results dispersibility | V | predicted results dispersibility |
|---|---|---|---|
| Spezial schwarz SS250 | 1 | 91.96 | 1 |
| Spezial schwarz SS100 | 1 | 15.79 | 1 |
| Printex G Cabot | 0 | −15.96 | 0 |
| Black pearl 2000 | 0 | −373.53 | 0 |
| Monarch 1000 | 0 | −30.40 | 0 |
| Monarch 700 | 0 | −159.13 | 0 |
| Mogul L | 0 | −19.33 | 0 |
| Elftex 485 | 0 | −133.94 | 0 |
| Elftex 285 | 0 | −79.02 | 0 |

The use of essentially non-stabilized colloidal carbon particles as a label in a method of determining in a test sample one or more components of the reaction between a specifically-binding protein and the corresponding bindable substance, has several advantages over and above the use of other labels. These advantages include a low cost price, ease of (bulk) preparation, light absorbance at a broad wavelength range, optimal features in view of contrast towards a light coloured background in e.g. solid phase-, dipstick- or agglutination (inhibition) sol particle (immuno-) assays and capability of adsorbing a wide range of totally differing binding proteins and/or bindable substances at the surface of the colloidal carbon particles.

In order to be able to develop assay systems which show controllable test performances in the way of sensitivity, specificity and reproduceability, it is important to have a thorough knowledge of the surface properties of the colloidal carbon-label particles.

Though the literature suggests the use of carbon particles as a label in immunoassays is taught (Peterson et al., Kang et al., Bergquist and Waller), none of these examples match the qualifications posed on the carbon particles, neither in the sense of carbon particle properties, nor in the sense of carbon particle size. All, Peterson et al., Kang et al., and Bergquist and Waller, show that prior to the supposed coupling of binding protein to the carbon particles in an aqueous medium, these particles must already have been stabilized by an amino acid like glycin (Peterson et al.), a polyalkylene glycol or a polysaccharide like dextran (Kang et al.), or other stabilizers like arabic gom and resins which is the case when India ink carbon particles are used (Bergquist and Waller). Without the addition of such stabilizers the carbon particles described by Peterson et al., Kang et al., and Bergquist and Waller do not form a stable, non-self agglutinating colloidal suspension in aqueous media such as pure water or buffer solutions of low ionic strength. These stabilized carbon aqueous sols of the prior art therefore need the addition or presence of stabilizing agents to the carbon particles in an aqueous medium prior to the addition of a specifically binding protein or the corresponding bindable substance.

The use of such stabilized carbon aqueous sols as a label system in immunoassays has several drawbacks:

Because the particles tend to agglutinate spontaneously, the sols are hard to handle.

There is no proof for an actual coupling of binding protein to the surface of the carbon particles. Both Peterson et al. and Bergquist and Waller use their stabilized carbon aqueous sols solely in an agglutination device. The formation of an antibody-antigen precipitate in the presence of suspended colloidal particles of the size 200–500 nm would force such (large) particles to co-precipitate anyway.

Because the surface of the carbon particles is first enveloped with an amino acid, a polyalkylene glycol, a polysaccharide like dextran, or a resin to stabilize the colloidal suspension in an aqueous medium, it is most likely that the binding protein will be hindered in coupling directly via hydrophobic interaction to the actual surface of the carbon particles in the following coupling step. In fact, Kang et al. need a time-consuming coupling step in which the binding protein is linked to the carbon label with the aid of an extra linking reagent. Such coupling procedures are tedious and will lead to varying, non-reproducable end results in respect of sensitivity and accuracy of the test methods.

Stabilized carbon aqueous sols are complex mixtures of stabilizing components and carbon particles in water with a large batch to batch variation. Due to this variation the handling of such sols is not straightforward and, from an economical point of view, at least unfavourable.

Treatment of the immunochemical carbon label with ionic or non-ionic surfactants (Kang et al.) can lead to reduced (immuno)reactivity (denaturation of binding protein, or decrease of the interaction forces between e.g. a sbp member and its corresponding bindable substance), or to desorption of immobilized bindable substances from the carbon particles.

The essentially non-stabilized carbon sol particles to be used according to the present invention have a number of advantages over the stabilized colloidal carbon particles and also over other colloidal particle labels. Surprisingly we found that it is very easy to produce stable colloidal carbon suspensions in aqueous media without any stabilizing agents or other components, i.e. non-stabilized carbon aqueous sols. Examples of suitable carbons are several channelblack/furnaceblack carbon types.

When used as a label in a method of determining in a test sample one or more components of the reaction between a specifically binding protein and the corresponding bindable substance, these non-stabilized carbon aqueous sols have several advantages over the stabilized carbon aqueous sols as described by Peterson et al., Kang et al., and Bergquist and Waller.

These advantages include:

The aforementioned carbons can form stable, colloidal suspensions in aqueous media such as pure water or buffers of low ionic strength by themselves, without the need of addition of complex mixtures of stabilizers (such as amino acids, resins or detergents), and preservatives.

The aforementioned carbons are delivered in prescribed, strictly defined size classes, covering the whole colloidal particle range, without any need for crude grinding of carbon, after purification using EDTA and HCl, in a mortar, as described by Peterson et al. In their initial stage of carbon-label preparation, also Kang et al. mention grinding of a mixture of raw carbon material and a stabilizing agent.

The aforementioned carbon starting material is available in very large bulk quantities; problems connected to batch to batch variation (like India ink, see Bergquist and Waller) are diminished. Therefore, reproduceability of carbon sols in respect of carbon surface properties and carbon particle size distribution has been found not to be a matter of concern.

The non-stabilized carbon aqueous sols are non-expensive, can easily be prepared in very large quantities, are very stable and therefore have a long shelf-life.

Due to the absence of any stabilizing agents in non-stabilized carbon aqueous sols before and during coupling of macromolecules (such as proteins, antigens, DNA/RNA) to the colloidal carbon particles, there is an actual, direct interaction between these macromolecules and all potential, active (e.g. hydrophobic) binding sites at the surface of the colloidal carbon particles.

Moreover, the conditions for coupling macromolecules onto colloidal carbon particles, via e.g. physical adsorption are known and can be strictly defined and controlled. (The composition of most India inks is not specified (Bergquist and Waller) and also the interactions between an amino acid like glycin, carbon particles and a binding protein remain more or less obscure (Peterson et al.)).

In conclusion it is very easy to couple macromolecules onto non-stabilized carbon aqueous sols. The resultant carbon/macromolecule conjugates give results which in terms of sensitivity, specificity and accuracy are not only reliable, but also very reproduceable.

The aforementioned carbons are delivered in prescribed, strictly defined size classes. The primary carbon particles preferably have average particle diameters ranging from 1 to approximately 100 nm. Due to the production/manufacturing process comprising heating, evaporating, burning and cracking of hydrocarbons used as a starting material, it might happen that during cooling some primary particles fuse together into larger, higher structured particles, called "secondary particles". The surface properties of primary and secondary particles of a specific carbon type are the same and as a consequence they behave similarly in view of their colloid-chemical stability in aqueous media such as water or buffers of low ionic strength. Preferably, the average particle size of the secondary particles does not exceed 400 nm. More preferably, the colloidal carbon particles have an average particle size within the range of from 1 to 200 nm.

These particle sizes of the non-stabilized carbon aqueous sols render them very suitable for application as a label in e.g. immuno-chromatographic assays. A preferred example of such an immunochromatographic assay is a dipstick assay in which the solid phase carrier (strip) consists of porous or fibrous materials such as natural or synthetic polymers and derivatives like nitrocellulose or nylon with pore sizes between 0.20 µm and 15 µm and a strip thickness of about 100 µm. On the strip, e.g. antibodies or antigens are immobilized by adsorption, absorption or covalent bonding. Sample materials containing an analyte specifically reactive with the immobilized member of the binding pair are applied to the carrier material and move chromatographically through the strip, where the analyte is immobilized by reaction with its corresponding binding pair member. The non-reacted sample materials are then removed by e.g. a washing step after which, in the case of a sandwich-type assay, the carbon-labelled reagent is applied to the carrier material.

Said carbon-labelled reagent is chromatographically easily mobile as a consequence of the relatively small carbon particle sizes and is capable of reaction with, and immobilization by the immobilized analyte.

The carbon-labelled reagent can be applied to the carrier material in a liquid form but, alternatively, it can be sprayed and dried onto a chromatographic medium in the presence of e.g. a meta-soluble protein and/or polysaccharide. In this case, the carbon-labelled reagent can be rapidly resolubilized in the presence of an appropriate solvent such as the sample or a chromatographic transport solvent.

Preparation and use of carbon sols

Production of non-stabilized carbon aqueous sols is very easy and non-expensive. After adding pure water or a buffer of low ionic strength to an amount of dry carbon powder, surprisingly a stable, black sol can be obtained by several methods such as for example by means of a sonifier. These non-stabilized (though stable!) carbon sols can be strongly diluted in water or buffers of low ionic strength. This diluted sol flocculates after adding an excess of NaCl and within a few minutes a black flocculated pellet and a clear, colorless supernatant are formed. This flocculation phenomenon can be used as a tool for monitoring physical adsorption of macromolecules onto carbon particles only in the case of non-stabilized carbon aqueous sols.

Addition of, for example, a suspension of a macromolecule in a buffer of low ionic strength to a diluted non-stabilized carbon aqueous sol will, under the proper conditions and after gentle mixing, result in coupling of the macromolecule onto the surface of the colloidal carbon particles via, amongst others, hydrophobic interaction. As a result of this macromolecule coating, the colloidal carbon particles will now be protected against flocculation by addition of an excess NaCl to the carbon/macromolecule-conjugate suspension.

In a systematic experimental set up in which increasing amounts of a certain macromolecule are incubated with a fixed amount of non-stabilized carbon aqueous sol under strictly defined and controlled conditions, addition of excessive amounts of NaCl will no longer lead to flocculation of the sol when a certain macromolecule/colloidal carbon particle ratio has been reached. This amount of macromolecule, the so called "minimal protective amount" (MPA) is an important parameter in the coupling procedure of macromolecules onto non-stabilized carbon aqueous sols and the value of the MPA depends amongst others on the nature of the macromolecule to be coupled, on the nature and amount of the colloidal carbon particles and on the coupling conditions in respect of pH and ionic strength.

Coupling of macromolecules to non-stabilized carbon aqueous sols can be ascertained therefore by performing a flocculation test and determination of the MPA, but can also be (double) checked by measurement of the light-absorbance of the supernatant after the carbon/macromolecule-conjugates have been pelleted by centrifugation. After addition of a minimal protective amount of a macromolecule to a non-stabilized carbon aqueous sol and a short incubation under proper conditions, repeated centrifugation of the carbon-macromolecule conjugates followed by repeated resuspending the successive pellets in an aqueous medium without any (other) macromolecule, addition of NaCl to the suspended pellet does still not cause flocculation. This indicates that an irreversible macromolecule-carbon bond has been formed.

This strong attachment of a macromolecule (e.g. an antibody) to the surface of the colloidal carbon particles makes non-stabilized carbon aqueous sols not only suitable to act as label in agglutination (inhibition) immunoassays, but makes them also very suited to act as signal generating label in all kinds of solid phase immunoassays, such as membrane chromatographic immunoassays. Considering application as a label in such chromatographic immunoassays, the relatively well defined particle size distribution of different species of non-stabilized carbon aqueous sols in the present invention is also an advantage over the non-stabilized carbon aqueous sols of Peterson et al. and Bergquist and Waller.

The homogenization step in the preparation of non-stabilized carbon aqueous sols is advantageously performed with ultrasonification, but can also be achieved by shaking or boiling (with or without stirring) a mixture of carbon particles and an aqueous medium without stabilizing agents.

Sonification of carbon powder in pure water or in a buffer of low ionic strength, followed by mixing this colloidal carbon suspension with a suspension of a macromolecule in (the same) buffer of low ionic strength under gentle mixing, is a simple, non-expensive and fast route towards the development of carbon-sol particle labels for all kinds of immunoassays.

Even addition of a suspension of a macromolecule (such as a protein) in a buffer of low ionic strength (final macromolecule amount at MPA-level) to a mixture of carbon powder and water during a (short) homogenization step by sonification leads to the formation of colloidal carbon-particle labels carrying said macromolecule, which in turn can be applied in immunoassays.

The immuno components labelled with carbon sol particles are used as reagents, commonly in combination with other reagents, for demonstrating and quantifying e.g. haptens, antigens, antibodies, and DNA/RNA in an aqueous test medium, e.g. body fluids such as blood plasma, serum and the like or culturing media of cells, for which all sorts of immunochemical techniques as are in use in radio-immunoassays and enzyme-immunoassays are suitable.

The invention accordingly also relates to test kits for use with such immunochemical techniques, and containing as the most important component an immuno component.

One of the conventional immunochemical techniques is the competitive immunoassay, which can be used for demonstrating and determining an immuno component. For demonstrating, for example, a certain antigen, this method comprises contacting a test sample containing an unknown amount of antigen with either a pre-determined quantity of the antigen in question, labelled with carbon and an insolubilized antibody against this antigen, or a pre-determined quantity of insolubilized antigen and an antibody directed against this antigen, labelled with carbon.

After completion of the reaction the quantity of the carbon is determined in the bound or free fraction, which can give a qualitative or a quantitative indication of the antigen to be determined. *Mutatis mutandis,* a similar method applies for determining other immuno components.

Other methods frequently being used are the so-called Sandwich techniques, which are also particularly suitable for the use of a component labelled with carbon according to the present invention. According to these techniques, an immunological component, for example, an antibody in case an antigen has to be determined, is insolubilized by coupling it to a solid carrier.

This solid carrier is, for example, the inner surface of the reaction vessel in which the immunochemical reaction is conducted. Also dipsticks on the basis of a nitrocellulose membrane or on the basis of a nylon membrane or polystyrene rods can be used as a solid phase carrier. After a first incubation, possibly followed by a washing step, a second incubation is effected with antibody labelled with carbon, whereafter said carbon is determined in the bound or the free phase.

The immuno components labelled with carbon also lend themselves well to the application in so-called homogeneous immunoassays, i.e. immunoassays in which a separation between the labelled immunological component bound in the immunochemical reaction and that which is still free is unnecessary. Such assays have the advantage of being simple to perform, providing the desired information relatively fast, and lending themselves excellently for automation.

In the actual assay, for example, test sample (or standard solution) containing the antigen to be determined is incubated together with the labelled antibody in the wells of a microtiter plate. The immunochemical reaction between antigen and (labelled) antibody will result in agglutination. The thus induced agglutination of the particles in a sol of carbon is accompanied by a change in light absorption, which can be monitored, e.g. spectrophotometrically or with the naked eye.

To determine small antigens, which in immunochemical respect are monovalent, use is made of an agglutination-inhibition reaction, which is based on the same principle.

In addition to the techniques mentioned above, there are countless other immunochemical techniques in which the immuno component labelled with carbon can be used as a reagent. Most preferably, however, the method of the invention is a solid phase immunoassay, more specifically an immunochromatographic assay, such as a dipstick immunoassay.

The analyte may be a soluble substance present in solution in a liquid test sample, or be exposed on the surface of cells in a test sample. Preferably, the analyte is selected from the group consisting of receptor proteins and epitopes present on the surface of cells, or, particularly in the case of liquid samples containing a soluble analyte in solution, is selected from the group consisting of haptens, antigens and antibodies.

Preferably, the binding component conjugated to the colloidal carbon particles is selected from the group consisting of haptens, antigens, antibodies, DNA and RNA.

The measurement of the nature and/or the concentration of the carbon in a certain phase of the reaction mixture can be effected according to numerous known techniques.

EXAMPLES

All steps described below are carried out at room temperature unless otherwise stated.

Preparation of carbon sols

Method A: ultra-sonification

Stock solution: 1 g carbon (Degussa, Special Black-4 RCC) is suspended in demineralized water to a final volume of 100 ml (1% (w/v)). The suspension is homogenized for 15 minutes by means of a Branson Model 250 Sonifier: Output control 3–27 Watt, 20 KHz (this sonification of the suspension can, optionally, occur on ice).

A deep black colloidal carbon suspension consisting of spherical carbon particles having an average primary particle diameter of 25 nm is formed. The stock-C-solution is kept at 4° C.

Method B: ultra-sonification

The procedure of Method A was applied to the Degussa, Special Black-250 LCF carbon.

A deep black colloidal carbon suspension consisting of spherical carbon particles having an average primary particle diameter of 56 nm is formed.

Method C: vortexing and differential centrifugation

Demi-water is added to 0.05 g carbon (Degussa, Special Black-4-RCC) to an end volume of 5 ml (1% w/v). The suspension is homogenized by vortexing for 10 minutes at 2500 rpm in a vortex mixer. The suspension is washed three times by centrifugation for 10 minutes at 13,800×g and resuspending the pellets each time in 5 ml demi-water. Finally, the suspension is centrifuged for 10 minutes at 1,000×g to remove aggregated colloidal carbon particles. The supernatant is decanted carefully and kept at 4° C.

In view of the loss of material occurring in the working-up of the suspensions, the carbon concentration is standardized to a spectrofotometric absorption of 1 at a wave length of 500 nm for a 1:15 dilution.

Method D: boiling and differential centrifugation

Demi-Water is added to 0.25 g carbon (Degussa, Special Black-4 RCC) to an end volume of 25 ml (1% w/v). While stirring with a magnetic stirrer, the suspension is gently boiled by 15 minutes in a closed glass vessel on a heating plate. After cooling to room temperature, the suspension is subjected to differential centrifugation in accordance with Method C.

Use of carbon sols

Example 1—Detection of human fibrinogen by means of a linear dilution series of goat anti-human fibrinogen antibodies spotted onto nitrocellulose strips.

Preparation of carbon particles-fibrinogen conjugate

Before use (for example, the physical adsorption of proteins) the stock carbon (C) suspension (made according to Method A) is diluted 5 times by means of 2.5 mM Tris-HCl, pH 8.5.

15 mg bovine fibrinogen, type i-s (Sigma) is dissolved in 5 ml of 2.5 mM Tris-HCl, pH 8.5=solution A.

15 mg human fibrinogen, fraction I (Sigma) is also dissolved in 5 ml of 2.5 mM Tris-HCl, pH 8.5—solution B.

5 ml of 0.2% (w/v) C-sol in 2.5 mM Tris-HCl, pH 8.5 are added to both 5 ml of solution A and 5 ml of solution B. The suspensions are incubated with stirring for 3 to 4 hours. Subsequently, the conjugates formed are washed 3 times by means of 5 mM NaCl, 1% (w/v) BSA, 0.02% (w/v) $NAN_3$, pH 8.5 by centrifugation at 13,636×g for 15 minutes. The first supernatant which is formed in each washing step is again centrifugated for 15 minutes at 13,636×g, after which the pellets are combined. This extra centrifugation serves to minimize the loss of material. After the third and last washing step the pellets are resuspended in half of the starting volume (the carbon concentration again is 0.2% (w/v)). The washed conjugates are kept in the dark at 4° C.

Preparation of the nitrocellulose strips with a linear dilution series of goat anti-human fibrinogen antibodies spotted thereon The following linear dilution series of polyclonal goat anti-human fibrinogen antibodies is spotted onto nitrocellulose membranes (Schleicher and Schuell, type BA 85/23 having a pore diameter of 0.45 µm): 1000 ng; 500 ng; 250 ng; 125 ng; 62 ng; 31 ng; 15 ng; 8 ng; 4 ng; 2 ng.

The series dilution is made with 10 mM PBS, pH 7.2. Per spot, 1 µl of solution is used; spot diameter<2 mm.

After application of the spots the membranes are air-dried for 3 hours. The free positions of the nitrocellulose are blocked by immersing the membranes for 1.5 hours at 37° C. in 10 mM PBS, 2% (w/v) BSA, 0.02% (w/v) $NAN_3$, pH 7.2. The membranes are air-dried again, whereafter they are affixed onto an adhesive plastic carrier material (Costar Serocluster platesealers) and finally cut to size (5×50 mm). The strips are kept dry in the dark and at room temperature.

Test Procedure

In stoppable polystyrene tubes (Greiner) of 4.5 ml, "goat antihuman fibrinogen strips" are incubated with:

| A | | B | |
|---|---|---|---|
| 1 ml | C-human fibrinogen conjugate | 1 ml | C-bovine fibrinogen conjugate |
| 500 µl | 2.5 mM Tris-HCl pH 8.5 | 500 µl | 2.5 mM Tris-HCl pH 8.5 |
| 500 µl | 20 mM Tris-HCl 600 mM NaCl 1% casein | 500 µl | 20 mM Tris-HCl 600 mM NaCl 1% casein |

| A | B |
|---|---|
| 0.2% (w/v) Tween-20 0.02% (w/v) $NaN_3$ pH 8.5 | 0.2% (w/v) Tween-20 0.02% (w/v) $NaN_3$ pH 8.5 |

After 5 minutes of incubation the strip in test A shows five clearly colored spots (1000–62 ng) decreasing in intensity. After 1.5 hours of incubation the spots have reached their maximum color intensities.

In Test B the strip does not show any colored spots.

Example II—Isotyping test for determining the isotype of monoclonal mouse immunoglobulins by means of monoclonal rat anti-mouse kappa/lambda (RAM k/λ) conjugate. Determination of the "minimal protective amount" (MPA) for monoclonal rat anti-mouse kappa/lambda (RAMκ/λ)-antibodies which are physically adsorbed onto colloidal carbon particles The minimal protective amount (MPA) is the minimal amount of a macromolecule that is necessary to protect one liter of a particular colloidal suspension against electrolytically induced flocculation by 14.3 g NaCl/l (end concentration). The MPA is dependent not only on the conditions in which coupling takes place, but also on the size of the molecule to be coupled and on the total available surface of all the particles that are present in one liter of a specific colloidal suspension.

The test is performed as follows:

The pH of the carbon sol (0.01% (w/v) Degussa Special Black-4 in 2.5 mM Tris-HCl, pH 10.5) is checked and, if necessary, adjusted at pH 10.5. A stock solution of RAMκ/λk-protein containing 0.94 mg/ml in 2.5 mM Tris-HCl, pH 10.5 is prepared and, using the same buffer, diluted so that a linear concentration range of 0–0.94 mg/ml RAMκ/λ-protein in 2.5 mM Tris-HCl, pH 10.5 is achieved. 500 µl of the carbon sol (0.01% (w/v) Degussa Special Black-4 in 2.5 mM Tris-HCl, pH 10.5) is added to 100µl of each RAMκ/λ-protein solution which is in turn thoroughly mixed with a vortex mixer. After an incubation period of 10 minutes, 100 µl 10% (w/v) NaCl solution is added to each carbon sol/protein suspension, which must be thoroughly mixed once again. Exactly 5 minutes after adding the 10% (w/v) NaCl solution, each sol/protein-suspension is screened visually for the appearance of black carbon clumps which tend to flocculate rapidly into/as a black pellet with a clear, colorless supernatant.

Controls of the test are:

1. 500 µl carbon sol+2×100 µl 2.5 mM Tris-HCl, pH 10.5 imitating a carbon sol which is completely protected by RAMκ/λ-protein.

2. 500 µl carbon sol+100 µl 12.5 mM Tris-HCl, pH 10.5+100 µl 10%(w/v) NaCl solution to determine the visual effects of complete flocculation on the appearance of the reaction mixture.

The results of this flocculation test show that at least 37.5 µg RAMκ/λ-protein is necessary to protect 500 µl of a 0.01%(w/v) Degussa Special Black-4 carbon sol in 2.5 mM Tris-HCl, pH 10.5 against flocculation by 14.3 g/l NaCl.

So, under the described coupling conditions the MPA for RAMκ/λ-protein would be 75 mg to adequately protect 1 liter (1000 ml!) 0.01%(w/v) Degussa Special Black-4 carbon sol in 2.5 mM Tris-HCl, pH 10.5 against an electrolytically induced flocculation.

Preparation of carbon particle-RAM conjugate

The stock carbon (C) solution (prepared according to method A) is diluted 100 times by means of demineralized water, after which the pH is set at 10.4 with 1M $K_2CO_3$ solution. Starting from a stock solution of RAM (Euroclone)

of 4.5 mg/ml in 20 mM Tris-HCl, 150 mM NaCl, pH 8.0, 167 μl RAM protein suspension are added to 10 ml sol (~75 μg RAM/ml carbon sol). The suspension is incubated with stirring for 60 minutes. Subsequently, the conjugate formed is washed 3 times by means of 2.5 mM Tris-HCl, 5 mM NaCl, 1% (w/v) BSA, 0.05% (w/v) NAN3, pH 8.5 by centrifugation at 13,800×g for 15 minutes. The washed conjugates are kept in the dark at 4° C.

Test procedure In stoppable polystyrene tubes (Greiner) of 4.5 ml HBT-subisotyping test strips (HBT, no. L10.10/ L10.20) are incubated with:

| A. | 500 μl | 20 mM Tris-HCl, 600 mM NaCl, 1% (w/v) casein, 0.2% (v/v) Tween-20, 0.02% (w/v) NaN₃, pH 8.5. |
|---|---|---|
|   | 500 μl | with 10 μg/ml IgG1 and 10 μg/ml IgG3 in RPMI (Gibco), 10% (v/v) fetal calf serum. |
|   | 1 ml | C-RAM conjugate |
| or |   |   |
| B. | 500 μl | 20 mM Tris-HCl, 600 mM NaCl, 1% (w/v) casein, 0.2% (v/v) Tween-20, 0.02% (w/v) NaN₃, pH 8.5. |
|   | 500 μl | RPMI (Gibco), 10% (v/v) fetal calf serum/ |
|   | 1 ml | C-RAM conjugate. |

After 5–30 minutes of incubation, meanwhile (carefully) continuously shaking the tubes containing the strips, the test result may be read:

Strip A shows a specific coloring of the spots at the positions 1.3 and kappa,

Strip B does not show any coloring.

Example III—One- and two-step test strip for determining human Chorionic Gonadotropin (hCG) by means of a (colloidal) carbon anti-hCG conjugate Preparation of carbon particles anti-α-hCG conjugate Method 1:

Before physically adsorbing the anti-α-hCG mouse monoclonal antibodies (MAB) the stock-C-suspension (made by method A) is diluted 5 times by means of 5 mM $KH_2PO_4$ buffer, pH 6.2.

To 1 ml of 0.2% (w/v) C-sol in 5 mM $KH_2PO4$ buffer, pH 6.2, 65 μl anti α-hCG MAB (750 μg anti-α-hCG MAB/ml sol) are added. The suspension is incubated for 3 hours with shaking. Subsequently, the conjugate formed is washed 3 times with 5 mM NaCl, 1% (w/v) BSA, 0.02% (w/v) $NAN_3$, pH 8.5 by centrifugation at 13,636×g for 15 minutes. The first supernatant which is formed in each washing step is again centrifugated for 15 minutes a 13,636×g, after which the pellets are combined. See also Example I. After the third and last washing step the pellet is resuspended in the starting volume. The washed conjugate is kept in the dark at 4° C.

Method 2:

Alternatively carbon particle anti-α-hCG conjugates can be prepared by adding 4 ml anti-α-hCG MAB (with 750 μg anti-α-hCG MAB/ml in 5 mM $KH_2PO_4$-buffer, pH 6.2) to 8 mg of dry carbon powder (e.g. Degussa Special Black-4 RCC). The suspension with 750 μg anti-α-hCG MAB/ml 0.2%(w/v) carbon particles is homogenized on ice for 1 minute by means of a Branson Model 250 Sonifier: Output control 3~27 Watt. 20 KHz.

A deep black, stable suspension of colloidal carbon particle/anti-α-hCG MAB-conjugates is formed. In order to remove any unbound anti-α-hCG MAB, the conjugates formed may be washed by centrifugation (see also method 1).

Preparation of nitrocellulose strips

Nitrocellulose strips are made with:

a. a linear dilution series of anti-β-hCG mouse monoclonal antibodies (MAB) spotted thereon.

b. a slot with rat anti-mouse monoclonal antibodies (negative test slot) and a slot with anti-β-hCG MAB (positive test slot) blotted thereon.

a. See Example I.

A linear dilution series of an anti-β-hCG MAB of 1000 ng; 500 ng; 250 ng; 125 ng; 62 ng; 31 ng; 15 ng; 8 ng; 4 ng; 2 ng in 10 mM PBS, pH 7.2 is spotted.

b. A slot with 1000 ng rat anti-mouse monoclonal antibodies and a slot with 500 ng anti-β-hCG MAB are blotted per row on nitrocellulose membranes (Schleicher and Schuell, type AE-99 having a pore diameter of 8.0 μm) by means of a vacuum slot-blot apparatus (PR-600, Hoefer Scientific Instruments). After blotting the membranes are air-dried for 3 hours.

The free positions of the nitrocellulose are blocked by immersing the membranes for 1.5 hours at 37° C. in 10 mM PBS, 2% (w/v) BSA, 0.02% (w/v) NAN3, pH 7.2. The membranes are air-dried again and then affixed onto an adhesive plastic carrier material (Costar Serocluster plate-sealers) and finally cut to size (10×75 mm).

The strips are kept dry in the dark and at room temperature.

Test procedure: Two-step method

First in vitro experiment

In stoppable polystyrene tubes (Greiner) of 4.5 ml a series of seven "anti-β-hCG strips" is pre-incubated with shaking with:

| 500 μl | 20 mM Tris-HCl, 600 mM NaCl, 1% (w/v) BSA, 0.2% (v/v) Tween-20, 0.02% (w/v) NaN₃, pH 8.5. |
|---|---|
| 500 μl | 2.5 mM Tris-HCl, pH 8.5 with such an amount of purified hCG (Sigma) that after combining said buffers the final concentration of the hCG is 50; 5; 1; 0.5; 0.1; 0.05 or 0 U/ml. |

After the pre-incubation the strips are rinsed 3 times with 10 mM PBS-T, pH 7.2 and once with demineralized water. The strips are post-incubated with:

| 500 μl | 20 mM Tris-HCl, 600 mM NaCl, 1% (w/v) casein, 0.2% (v/v) Tween-20, 0.02% (w/v) NaN₃, pH 8.5. |
|---|---|
| 500 μl | 2.5 mM Tris-HCl, pH 8.5 |
| 1 ml | C sol anti-β-hCG conjugate |

With the hCG concentrations (50–0.1 U/ml), the first four spots occur after about five minutes. After 1 hour of incubation, the strip with:

| 50 U/ml hCG | shows 7 spots decreasing in intensity; |
|---|---|
| 5 U/ml hCG | shows 5 spots decreasing in intensity; |
| 1 U/ml hCG | shows 4 spots decreasing in intensity; |
| 0.5 U/ml hCG | shows 4 spots decreasing in intensity; |
| 0.1 U/ml hCG | shows 4 spots decreasing in intensity; |
| 0.05 U/ml hCG | shows 4 spots all having a low intensity; and |
| 0 U/ml hCG | shows no spots at all. |

Second in vivo experiment

In stoppable polystyrene tubes (Greiner) of 4.5 ml two "anti-β-hCG strips" are pre-incubated with shaking with (control strip):

| 250 μl | 2.5 mM Tris-HCl, pH 8.5 |
|---|---|
| 250 μl | 20 mM Tris-HCl, 600 mN NaCl, 1% (w/v) BSA, 0.2% (v/v) Tween-20, 0.02% (w/v) NaN₃, pH 8.5 |
| 500 μl | urine of a non-pregnant woman 4 weeks before conception; and with (test strip): |

-continued

| 250 μl | 2.5 mM Tris-HCl, pH 8.5. |
| --- | --- |
| 250 μl | 20 mM Tris-HCl, 600 Mm NaCl, 1% (w/v) BSA, 0.2% (v/v) Tween-20, 0.02% (w/v) NaN$_3$, pH 8.5 |
| 500 μl | urine of the same woman as in the negative test, but this time 16 days after conception. |

After the pre-incubation the strips are rinsed 3 times with 10 mM PBS-t, pH 7.2 and once with demineralized water. The strips are post-incubated with:

| 500 μl | 2.5 mM Tris-HCl, 600 mM NaCl, 1% (w/v) casein, 0.2% (v/v) Tween-20, 0,02% (w/v) NaN$_3$, pH 8.5. |
| --- | --- |
| 500 μl | 2.5 mM Tris-HCl, pH 8.5. |
| 1 ml | C-sol anti-α-hCG conjugate. |

After a few minutes 3 spots occur on the test strip incubated with urine after the conception, the control strip does not show any spots even after incubating overnight.

Test procedure: One-step method

Two nitrocellulose strips (Schleicher and Schuell, type AE99) with slots of RAM and anti-α-hCG MAB are pre-wetted on the place of application with 10 μl 10 mM PBS-T, 1% (w/v) BSA, 0.02% (w/v) NAN$_3$, pH 7.2 (=running liquid) after which 10 μl C-sol anti-α-hCG conjugate is immediately applied on the same place of application.

Subsequently, the strips are immersed with the side on which the place of application is situated in glass vessels containing 2 ml running liquid with 40 U/ml hCG (positive test), 2 ml running liquid with 5 mU/ml hCG (positive test), and 2 ml running liquid without hCG (negative test), respectively. When the liquid front has passed the entire length of the strip (this takes about 3–5 minutes), the positive test strips show a black coloring of both the RAM slot and the anti-β-hCG slot, while on the negative test strip only the RAM slot is colored.

We claim:

1. A method for determining the presence or amount of an analyte in a sample comprising contacting said sample with a labeled constituent consisting of an aqueous carbon sol which is stable in the absence of a stabilizing substance, said sol having directly conjugated to the surface of the colloidal carbon particles a binding component which specifically binds said analyte, and determining the presence or absence of a resulting analyte/carbon particle complex as an indication of the presence or a measure of the amount of analyte in said sample, wherein the carbon grade used satisfies the condition V>0 wherein V is a linear predictor value according to the formula $V=-138.954-0.987 \times DBP+15.609 \times VC+3.994 \times PPD$, wherein DBP is the dibutylphthalate adsorption in ml/100 g, as determined according to DIN 53601; VC is the volatile content in %, as determined according to DIN 53552; and PPD is the average primary particle diameter in nanometers.

2. The method of claim 1 wherein the analyte is selected from the group consisting of receptor proteins and epitopes present on the surface of cells.

3. The method of claim 1 wherein the analyte is selected from the group consisting of haptens, antigens and antibodies.

4. The method of claim 1 wherein the binding component conjugated to the colloidal carbon particles is selected from the group consisting of haptens, antigens, antibodies, DNA and RNA.

5. The method of claim 1 which is a solid phase immunoassay.

6. The method of claim 1 which is an immunochromatographic assay.

7. The method of claim 1 which is a dipstick immunoassay.

8. The method of claim 1 wherein the primary colloidal carbon particles have an average particle size within the range of from 1 to 100 nm.

9. The method of claim 1 wherein said aqueous carbon sol does not contain sol-stabilizing agent.

* * * * *